(12) United States Patent
Schut et al.

(10) Patent No.: US 9,468,186 B2
(45) Date of Patent: Oct. 18, 2016

(54) TOMATO SPOTTED WILT VIRUS AND/OR IMPATIENS NECROTIC SPOT VIRUS RESISTANCE IN CULTIVATED LETTUCE

(71) Applicant: RIJK ZWAAN ZAADTEELT EN ZAADHANDEL B.V., De Lier (NL)

(72) Inventors: Johannes Wilhelmus Schut, Wouw (NL); Arnaud Paul Pierre Thabuis, Montfavet (FR); Marc Villevieille, Avignon (FR)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 130 days.

(21) Appl. No.: 14/211,989

(22) Filed: Mar. 14, 2014

(65) Prior Publication Data
US 2014/0289907 A1    Sep. 25, 2014

Related U.S. Application Data

(63) Continuation-in-part of application No. 13/836,281, filed on Mar. 15, 2013, now abandoned.

(30) Foreign Application Priority Data

Mar. 15, 2013  (EP) .................................. 13159628

(51) Int. Cl.
*A01H 5/12*  (2006.01)

(52) U.S. Cl.
CPC ...................................... *A01H 5/12* (2013.01)

(58) Field of Classification Search
None
See application file for complete search history.

(56) References Cited

PUBLICATIONS

NCBI Blast results of SEQ ID Nos. 1 and 2.*
Wintermantel and Simko, Development of methods for maintenance of lettuce-infecting tospoviruses, effective germplasm screen, and identification of sources of resistance, Aug. 1, 2014.*
Ales Lebeda, et al. "Wild Lactuca germplasm for lettuce breeding: current status, gaps and challenges" Euphytica 170(1-2):15-34, Mar. 2009.
J.J. Cho, et al. "Conventional Breeding: Host-Plant Resistance and the Use of Molecular Markers to Develop Resistance to Tomato Spot Wilt Virus in Vegetables" Acta Horticulturae 431:367-378, Jan. 1996.
P.J. O'Malley et al. "Resistance to Tomato Spotted Wilt Virus in Lettuce" HortScience 24(2):360-362, Apr. 1989.
M L Thomas-Carroll, et al. "Selection, biological properties and fitness of resistance-breaking strains of Tomato spotted wilt virus in pepper" Annals of Applied Biology 142(2):235-243, Apr. 2003.
M. Wang, et al. "Identification and incorporation of TSWV resistance into commercial lettuce",82(10):1087, Aug. 1992.
CGN Trait Information—Trait Information for Tomato Spotted Wilt Virus dated Jun. 9, 2016, retrieved from www.cgngenis.wur.nl/traitinfo.aspx?Cropnumber=06&Traitnumber=30.

* cited by examiner

*Primary Examiner* — Eileen B O Hara
(74) *Attorney, Agent, or Firm* — Vedder Price P.C.; Thomas J. Kowalski; Deborah L. Lu

(57) ABSTRACT

The invention relates to a lettuce plant (*Lactuca sativa* L.), which may comprise a genetic determinant, which confers resistance to tomato spotted wilt virus (TSWV) and/or impatiens necrotic spot virus (INSV), and which is as found in plants grown from seeds of which a representative sample was deposited under NCIMB accession number NCIMB 42023. The invention further provides seeds, progeny, propagation material and food products from the plant.

14 Claims, No Drawings

TOMATO SPOTTED WILT VIRUS AND/OR IMPATIENS NECROTIC SPOT VIRUS RESISTANCE IN CULTIVATED LETTUCE

RELATED APPLICATIONS AND INCORPORATION BY REFERENCE

This application is a continuation-in-part application of U.S. patent application Ser. No. 13/836,281 filed Mar. 15, 2013 and claims benefit of and priority to European patent application Serial No. 13159628.0 filed Mar. 15, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to lettuce (*Lactuca sativa* L.) plants resistant against tomato spotted wilt virus (TSWV) and/or impatiens necrotic spot virus (INSV). The invention further relates to parts of these plants, to seeds, to propagation material, to the progeny of these plants and use of the plants as germplasm in breeding for TSWV/INSV resistance.

BACKGROUND OF THE INVENTION

Cultivated lettuce belongs to the highly polymorphic species, *Lactuca sativa*, which is a member of the Asteraceae (Compositae) family. *L. sativa* is one of approximately 300 species in the genus *Lactuca*. Lettuce is related to chicory, sunflower, aster, acorzonera, dandelion, artichoke and chrysanthemum. Lettuce is commercially grown for its edible head and leaves, wherever environmental conditions permit the production of an economically viable yield.

TSWV and INSV are closely related but distinct members of the genus *Tospovirus*. Since viruses such as TSWV and INSV are obligate parasites, they are unable to survive outside of their host species. Transmission of these viruses occur from one plant to another by seed, insects or cuttings. Six *thrips* species are known TSVW vectors: Western flower *thrips*, onion *thrips* (*Thrips tabaci*), tobacco *thrips* (*Frankiniella fusca*), common blossom *thrips* (*Frankliniella schultzei*), *Thrips setosus*, and *Scirtothrips dorsalis*. In the case of INSV, the insect vector is Western flower *thrips* (*Frankliniella occidentalis*). Both viruses are highly polyphagous and can cause total crop losses in a number of cultivated vegetable crops including lettuce, tomato, and pepper. In lettuce, TSWV and/or INSV infection has been confirmed on cos or romaine, crisphead or iceberg, and greenleaf lettuces, but essentially these viruses are capable of infecting all types of lettuces.

Symptoms of TSWV and INSV may vary depending on the host, environmental conditions affecting the host, and the individual virus infecting the plant. Common symptoms that may affect all hosts include necrotic spots, streaking, ring spots, stunting, and wilting.

In lettuce, TSWV and/or INSV can cause indistinguishable symptoms. The leaves of infected lettuce plants develop brown spots and necrotic areas. As necrosis spreads, much of the leaf browns, dries out, and dies. Margins of leaves may wilt and become yellow. Leaf browning and yellowing is evident on both newer and older leaves. Often only one side of an infected plant is affected. Lettuce plants that are infected early in development may become stunted and then die. Infected plants that survive to harvest are usually unmarketable. Additionally, TSWV infected lettuce plants produce limited or no seeds. Diagnosis is difficult based on symptoms alone, as these may resemble other fungal and bacterial diseases, damage caused by fertilizer or pesticide applications, or environmental stresses.

Currently, methods to control TSWV and INSV are mainly targeted towards the *thrips* vectors, or may involve the application of sanitation measures. TSWV and INSV may be controlled with good management practices that reduce the likelihood of *thrips* infestation, inspecting and isolating plants that present virus symptoms and/or *thrips*, destroying such symptomatic plants, and monitoring and managing *thrips* levels. Although chemical control of *thrips* is possible, repeated use of certain insecticides has led to resistant *thrips* populations. Therefore, it is highly advantageous to find direct sources of resistance to TSWV and/or INSV, rather than managing the virus vectors or employing control measures once infectivity has already set in.

One approach to introduce TSWV resistance to lettuce is through genetic engineering. Transgenic lettuce plants expressing the nucleocapsid (N) protein gene of the lettuce isolate of TSWV were protected against TSWV isolates. Resistance occurs either through accumulation of high levels of transgenic N protein or by an N transgene silencing mechanism activated by its overexpression. Although transgenic methods for introducing resistance may prove to be effective, under the current environment it may not be a widely accepted method, especially when the end product will be used for food consumption.

Citation or identification of any document in this application is not an admission that such document is available as prior art to the present invention.

SUMMARY OF THE INVENTION

The present state of the art does not provide for lettuce plants that are resistant against TSVW and/or INSV. It therefore is the object of the present invention to develop lettuce plants that are resistant against TSVW and/or INSV, and herein display agronomically desirable traits. In the research that led to the present invention, novel lettuce plants (*Lactuca sativa* L.) were developed such that they are highly resistant against TSVW and/or INSV.

The said resistance of the invention is controlled by a genetic determinant, the inheritance of which is consistent with that of a monogenic recessive trait. The term "recessive" is to mean in this context that the fully achievable resistance is only observable in plants which may comprise the genetic determinant in the homozygous state.

Since the inheritance of the resistance is comparable to that of a monogenic trait, it has an advantage over the prior art, because the resistance is high, can easily be incorporated into various cultivated lettuce types, and is directed against TSWV and/or INSV.

The present invention relates to a lettuce plant which may comprise a genetic determinant, which when homozygously present confers high resistance to TSWV and/or INSV, and which is as found in, or present in, or contained in, or obtainable from the genome of plants grown from seeds of which a representative sample was deposited under NCIMB accession number NCIMB 42023.

The invention further relates to a lettuce plant which may comprise the genetic determinant homozygously, and thus is highly resistant against TSWV and/or INSV.

In one embodiment, the invention provides a lettuce plant that is resistant against TSWV and/or INSV, obtainable by crossing a resistant plant of which representative seed was deposited under NCIMB accession number NCIMB 42023 with another lettuce plant to produce an F1, subsequently selfing said F1 to obtain an F2, and selecting a plant that shows resistance to TSWV and/or INSV.

Furthermore, it was found during the research leading to the present invention that the genetic determinant conferring resistance to TSWV and/or INSV, is located on linkage group 2 of the integrated genetic linkage map of lettuce (Truco et. al. (2007) Theoretical and Applied Genetics, 115(6): 735-46) and linked to marker TSWV-00001 (SEQ ID NO: 1).

More in particular, in the deposit NCIMB 42023 the genetic determinant conferring resistance to TSWV and/or INSV is located on linkage group 2 of the integrated genetic linkage map of lettuce between markers TSWV-00001 (SEQ ID NO: 1) and TSWV-00002 (SEQ ID NO: 2).

The invention also relates to a lettuce plant resistant against TSWV and/or INSV, which may comprise a genetic determinant that confers resistance to TSWV and/or INSV, wherein said genetic determinant is obtainable by introgression from a plant grown from seeds of which a representative sample was deposited under NCIMB accession number NCIMB 42023, and wherein said genetic determinant in the seeds of the seed deposit number NCIMB 42023 is a position on linkage group 2 and linked to marker TSWV0000-1.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of and "consists essentially of have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with NCIMB, under deposit accession number 42023 were made pursuant to the terms of the Budapest Treaty. Upon issuance of a patent, all restrictions upon the deposit will be removed, and the deposit is intended to meet the requirements of 37 CFR §1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

A lettuce plant carrying the genetic determinant conferring resistance to TSWV and/or INSV can be suitably identified amongst descendants from a cross between a plant susceptible to TSWV and/or INSV, and a plant that carries the genetic determinant, preferably in the homozygous state, by growing F2 plants from seeds that are the result of the initial cross and a selfing step, and selecting plants showing the resistance trait. Plants can be selected on the basis of determining phenotype through a bioassay, or through the identification of the genetic determinant, for example by means of one or more of the markers defined herein.

A bioassay, is a testing method that is capable of discerning between plants that are susceptible or resistant against a particular pathogen. A TSWV or INSV bioassay as used herein, is performed by firstly sowing seeds of the plants to be tested, preferably on peat cubes in a glass house, and growing the seeds into plants. The plants are grown, preferably for 2 weeks, and preferably at a temperature between 22° C. to 28° C. A relevant number of plants per line are evaluated, preferably about 14 plants, to allow for segregation to be observed if present.

When plants are preferably at growth stage 3 or 4, they are inoculated, preferably by mechanical inoculation, with an inoculum containing the appropriately maintained viral pathogen. TSWV inoculated plants are scored for infection, preferably at 14 days and 21 days post-infection, while INSV inoculated plants are scored for infection, preferably at 18 days, 24 days, and 30 days post-infection. Suitable resistant and susceptible plants, if available, can be included as control plants in the bioassay.

Resistance or susceptibility to the pathogen, is scored on an appropriate scale, based on the plant's symptoms, or lack thereof, to the pathogen. The skilled person can use a scale with any subdivision as long as the scoring is performed at the same plant growth stage as used herein. The results of the TSWV and/or INSV bioassay may be confirmed, preferably in field tests where the corresponding disease pressure is present. Disease scoring in the field test is performed preferably using the same scale for scoring symptoms as was used for the bioassay. Additionally, ImmunoStrip tests (Agdia Inc., Elkhart, Ind., USA, 46514) for TSWV and INSV for example, can be used to confirm that those plants that are scored as being symptomless or resistant in the bioassays, also prevent viral multiplication or the accumulation of virus particles, following virus inoculation of the plant.

The method of mechanical inoculation with a virus is well known in the art. Mechanical inoculation involves rubbing cotyledons of the plant to be infected, with the viral inoculum. For TSWV, the inoculum used for mechanical inoculation is prepared by grinding young leaves showing visible signs of infection, preferably using a mixture of TSWV infected *Nicotiana benthamiana* leaves (1/5$^{th}$) and two TSWV infected lettuce cultivars (each 2/5$^{th}$s), in a freshly prepared inoculation buffer, with carborundum and charcoal. Similarly for INSV, the inoculum used for mechanical inoculation is prepared by grinding young leaves showing visible signs of infection, preferably using a mixture of INSV infected *Nicotiana benthamiana* leaves (1/2) and two INSV infected lettuce cultivars (each 1/4), in a freshly prepared inoculation buffer, with carborundum and charcoal. Following viral inoculation, plants are rinsed with distilled water and maintained in the greenhouse.

Mechanical inoculation is used both for the TSWV and INSV bioassays, and for the multiplication of TSWV and INSV. Maintaining the virulence of these pathogens for inoculation is important for the efficacy of the bioassay. For both TSWV and INSV, the method used for virus multiplication is adapted from Marchoux et al. 2008 (Virus des Solanacées. Du génome viral a la protection des cultures. Versailles (FRA): Editions Quae; Syntheses. 2008: 615-624). The virus is multiplied by mechanical inoculation with a wildtype TSWV or INSV strain collected from TSWV- or INSV-infected lettuce in the field. Viral multiplication of TSWV is performed, preferably in *N. benthamiana* plants and two different lettuce cultivars, every 7 to 12 days, most preferably every 10 days, while the multiplication of INSV is performed, preferably in *N. benthamiana* plants and two different lettuce cultivars, preferably every 6 days. Plants in which the virus is to be maintained are mechanically inoculated as described for the bioassay. The aggressiveness of the viral inoculum is regularly tested using known susceptible controls. If the inoculum is showing reduced aggressiveness (i.e. reduced or no symptoms) on the susceptible controls, then a new wild TSWV strain or wild INSV strain from the field is multiplied and maintained for each bioassay respectively.

In the absence of molecular markers or in the event that recombination between the molecular markers and the genetic determinant have taken place and these are not predictive anymore, equivalence of genetic determinants can still be determined by an allelism test. To perform an allelism test, material that is homozygous for the known determinant, a tester plant, is crossed with material that is homozygous for the genetic determinant that is to be tested. This latter plant is referred to as the donor plant. The donor plant to be tested should be or should be made homozygous for the genetic determinant to be tested. The skilled person is aware of how to obtain a plant that is homozygous for the genetic determinant to be tested. When in the F2 of the cross between a donor plant and a tester plant, no segregation for the phenotype related to the genetic determinant is observed, the genetic determinants of the donor plant and the tester plant have been proven to be equivalent or the same.

The invention also relates to a lettuce plant that may comprise a genetic determinant conferring resistance to TSWV and/or INSV, wherein plants of the first generation progeny (F1) of a cross of the said plant with a tester plant, that may comprise the said genetic determinant and of which representative seed was deposited with the NCIMB under accession number NCIMB 42023, or a progeny plant thereof that may comprise the said genetic determinant, or a plant derived there from and which may comprise the said genetic determinant, show a 1:0 segregation for the resistance to TSWV and/or INSV. In both the tester plant and the plant of the invention, the genetic determinant is present in homozygous form. Plants of the second and further generations, if obtained by selfing also show a 1:0 segregation for the said resistance pattern. The tester plant can be a plant of which representative seed was deposited with the NCIMB under accession number NCIMB 42023.

The lettuce plant of the invention can be any one of the types of cultivated lettuce from the following group: iceberg or crisphead, butterhead, romaine or cos, green leaf, red leaf, lollo, oakleaf, curly, incised leaf, multileaf, cutting, stem, Batavia, and Latin lettuce.

In another embodiment, the invention relates to seeds which may comprise the said genetic determinant conferring resistance to TSWV and/or INSV. A plant grown from the seeds is resistant against TSWV and/or INSV when the genetic determinant is present in the homozygous state.

The invention further relates to seeds which may comprise said genetic determinant and which seeds are capable of growing into plants that are resistant against TSWV and/or INSV.

The invention also relates to progeny of the plants, cells, tissues, and seeds of the invention. Such progeny can in itself be plants, cells, tissues, or seeds.

The term "progeny" used herein is intended to mean the first and all subsequent descendants from a cross with a plant of the invention that may comprise the said genetic determinant. "Progeny" also encompasses plants that carry the trait of the invention and are obtained from other plants or progeny of plants of the invention by vegetative propagation or multiplication.

Thus in one embodiment, the invention relates to progeny of a lettuce plant which may comprise the genetic determinant of the invention.

In a further embodiment, the invention relates to progeny of lettuce plants of the invention that are resistant against TSWV and/or INSV. These progeny plants thus may comprise the genetic determinant conferring resistance to TSWV and/or INSV, preferably in homozygous form.

According to a further aspect thereof, the invention relates to propagation material capable of growing into a plant of the invention.

In one embodiment, such propagation material is formed by a seed of the lettuce plant of the invention, wherein the plant that can be grown from the seed may comprise a genetic determinant of the invention.

In a further embodiment, the propagation material capable of growing into a plant of the invention is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

In an additional embodiment, the invention relates to tissue culture of propagation material capable of growing into a plant of the invention.

In another embodiment, the plant produced from the propagation material may comprise the genetic determinant as found in the genome of lettuce plants grown from seeds, and of which representative seed was deposited under NCIMB accession number NCIMB 42023.

Lettuce destined for the fresh and processing industry, and thus for human consumption, need to be free from disease. Moreover, disease symptoms caused by TSWV and/or INSV infection can lead to a significant reduction of both the yield and quality of lettuce that is harvested, since infected plants that survive to harvest are usually unmarketable. Outbreaks of TSWV and INSV are notoriously difficult to manage. Disease and pest control measures aimed at the *thrips* vector of TSWV and INSV (e.g. insecticides; e.g. sanitation measures) can significantly add to the cost of lettuce production, and this cost also translates to the harvested or processed end product. It is thus highly relevant for the fresh and processing industry to grow and harvest lettuce plants that are resistant to TSWV and/or INSV, since such resistant plants will give higher yields and better quality product as compared to the same lettuce plants lacking the aforementioned resistance(s).

The invention therefore relates to the harvested part of the lettuce plant which may comprise the genetic determinant conferring resistance to TSWV and/or INSV.

Moreover, the invention relates to a food product which may comprise one or more harvested parts of a lettuce plant which may comprise the genetic determinant conferring TSWV and/or INSV resistance. The harvested part or food product may be, or may comprise the lettuce head and/or leaves of a lettuce plant. A preferred food product which may comprise parts of the lettuce plant of the invention is a salad, wherein the lettuce leaves may optionally be mixed with other leaves of for example spinach, endive, chicory, beet, Swiss chard, etc.

The food product or harvested part may have undergone one or more processing steps. Such a processing step might comprise but is not limited to any one of the following treatments or combinations thereof: cutting, washing, grilling, stir-frying, or a salad mixture which may comprise leaves of the lettuce plant of the invention. The processed form that is obtained is also part of this invention.

The processed lettuce may also be used in another food product, such as a soup, a sandwich, etc. Such food products may be pre-packed and intended for sale in a supermarket. The invention thus also relates to the use of lettuce plants of the invention or parts thereof in the preparation of food products, in particular salads, soups, and sandwiches.

Another aspect of this invention relates to a nucleic acid molecule which is causative of resistance to TSWV and/or INSV. The said DNA molecule may comprise a DNA sequence which is linked to marker TSWV-00001 positioned on linkage group 2. The nucleic acid molecule is also part of this invention.

In one embodiment, the nucleic acid molecule which is causative of resistance to TSWV and/or INSV is located between markers TSWV-00001 (SEQ ID NO: 1) and TSWV-00002 (SEQ ID NO: 2). The nucleic acid molecule is also part of this invention.

Yet another aspect of the invention relates to use of the markers and said nucleic acid molecule to identify plants which are resistant against TSWV and/or INSV, and/or carrying the genetic determinant conferring resistance to TSWV and/or INSV.

Therefore in one embodiment the invention relates to the use of marker TSWV-00001 (SEQ ID NO: 1), or the said DNA molecule which may comprise a DNA sequence which is positioned on linkage group 2, or part thereof, to identify plants resistant against TSWV and/or INSV, and/or carrying the genetic determinant conferring resistance to TSWV and/or INSV.

In another embodiment the invention relates to the use of marker TSWV-00001 (SEQ ID NO: 1), or the said DNA molecule which may comprise a DNA sequence which is positioned on linkage group 2 between markers TSWV-00001 and TSWV-00002, or part thereof, to identify plants resistant against TSWV and/or INSV, and/or carrying the genetic determinant conferring resistance to TSWV and/or INSV.

The skilled person knows how to develop new markers linked to a trait using already known markers, QTLS, alleles, genes or other DNA molecules that are associated with a certain trait.

Thus, the invention also relates to the use of marker TSWV-00001 (SEQ ID NO: 1), and the said DNA molecule, or part thereof, for developing other markers linked to the genetic determinant conferring resistance to TSWV and/or INSV.

In one aspect the invention relates to a process for producing lettuce plants which may comprise a genetic determinant that confers resistance to TSWV and/or INSV, which may comprise the step of selecting said lettuce plants from a population of lettuce plants segregating for the said genetic determinant using marker TSWV-00001 (SEQ ID NO: 1).

The term "genetic determinant" as used herein encompasses one or more QTLs, genes, or alleles. These terms are used interchangeably. A genetic determinant can alternatively be identified by the position on a genetic map, or by indication of the location on a linkage group or chromosome. When a genetic determinant is no longer linked to a specific molecular marker, but its position on a chromosome as defined on a genetic map is unaltered, this genetic determinant is still the same as when it was linked to the molecular marker. The genetic trait that it confers is therefore also still the same.

The invention further relates to a cell of a lettuce plant of the invention, which cell may comprise a genetic determinant which leads to resistance to TSWV and/or INSV, wherein the said genetic determinant is as present in a lettuce plant, representative seeds of which were deposited under NCIMB accession number NCIMB 42023. The said cell thus may comprise the genetic information encoding the said resistance to TSWV and/or INSV, in particular genetic information which is substantially identical, preferably completely identical to the genetic information encoding the said resistance to TSWV and/or INSV, representative seeds of which were deposited under NCIMB accession number NCIMB 42023. Preferably, the cell of the invention is part of a plant or plant part, but the cell may also be in isolated form.

The invention also relates to a cell of a lettuce plant of the invention, which cell may comprise a genetic determinant which leads to resistance to TSWV and/or INSV, and which plant is obtained by transferring the said resistance, as found in seeds of which a representative sample was deposited under NCIMB accession number NCIMB 42023 into an agronomically valuable lettuce plant.

The invention further relates to seed of the lettuce plant of the invention, which seed contain in their genome the genetic information that encodes the resistance to TSWV and/or INSV.

The invention also relates to the use of seeds of which a representative sample was deposited under NCIMB accession number NCIMB 42023 for transferring the resistance to TSWV and/or INSV into another agronomically valuable lettuce plant.

The invention also relates to the use of a lettuce plant of the invention that exhibits resistance to TSWV and/or INSV due to the presence, in the genome of the plant, of the said resistance as found in seeds of which a representative sample was deposited under NCIMB accession number NCIMB 42023, as a crop.

The invention also relates to the use of a lettuce plant of the invention that exhibits resistance to TSWV and/or INSV due to the presence, in the genome of the plant, of the said resistance as found in seeds of which a representative sample was deposited under NCIMB accession number NCIMB 42023, as a source of seed.

The invention also relates to the use of a lettuce plant of the invention that exhibits resistance to TSWV and/or INSV due to the presence, in the genome of the plant, of the said resistance as found in seeds of which a representative sample was deposited under NCIMB accession number NCIMB 42023, as a source of propagating material.

The invention also relates to the use of a lettuce plant of the invention that exhibits resistance to TSWV and/or INSV due to the presence, in the genome of the plant, of the said resistance as found in seeds of which a representative sample was deposited under NCIMB accession number NCIMB 42023, for consumption.

In one aspect the invention relates to a method for producing a lettuce plant resistant against TSWV and/or INSV, which may comprise:

a) crossing a plant which may comprise a genetic determinant that leads to resistance to TSWV and/or INSV with another plant;
b) selfing the resulting F1 for obtaining F2 plants;
c) selecting plants resistant against TSWV and/or INSV in the F2;
d) optionally performing one or more additional rounds of selfing or crossing, and subsequently selecting for a plant which may comprise the trait.

The word "trait" in the context of this application refers to the phenotype of the plant. In particular, the word "trait" refers to the trait of the invention, more in particular to the resistance to TSWV and/or INSV. The term "genetic determinant" is used for the genetic information in the genome of the plant that causes the trait of the invention. When a plant shows the trait of the invention, its genome may comprise the genetic determinant causing the trait of the invention. The plant thus has the genetic determinant of the invention.

It is clear that the parent that provides the trait of the invention is not necessarily a plant grown directly from the deposited seeds. The parent can also be a progeny plant from the seed or a progeny plant from seeds that are identified to have the trait of the invention by other means.

In one embodiment the invention relates to a method for producing a lettuce plant resistant against TSWV and/or INSV, which may comprise:

a) crossing a plant which may comprise a genetic determinant that leads to resistance to TSWV and/or INSV with another plant;
b) optionally backcrossing the resulting F1 with the preferred parent;
c) selecting for plants that are resistant against TSWV and/or INSV in the F2;
d) optionally performing one or more additional rounds of selfing or crossing, and subsequently selecting for a plant which may comprise said resistance to TSWV and/or INSV.

The present invention additionally provides a method for introducing another desired trait into a lettuce plant resistant against TSWV and/or INSV, which may comprise:

a) crossing a lettuce plant resistant against TSWV and/or INSV, representative seeds of which were deposited under deposit number NCIMB 42023, with a second lettuce plant that may comprise a desired trait to produce F1 progeny;
b) selecting an F1 progeny that may comprise said resistance to TSWV and/or INSV and the desired trait;
c) crossing the selected F1 progeny with either parent, to produce backcross progeny;
d) selecting backcross progeny which may comprise the desired trait and resistance to TSWV and/or INSV; and
e) optionally repeating steps c) and d) one or more times in succession to produce selected fourth or higher backcross progeny that may comprise the desired trait and resistance to TSWV and/or INSV. The invention includes a lettuce plant produced by this method.

In one embodiment, selection for plants resistant against TSWV and/or INSV is done in the F1 or any further generation by using marker TSWV-00001 (SEQ ID NO: 1). In another aspect selection for the trait of the invention is started in the F2 of a cross or alternatively of a backcross. Selection of plants in the F2 can be done phenotypically as well as by using the said marker(s) which directly or indirectly detect(s) the genetic determinant underlying the trait.

In one embodiment, selection for plants resistant against TSWV and/or INSV is started in the F3 or a later generation.

In one embodiment the plant which may comprise the genetic determinant is a plant of an inbred line, a hybrid, a doubled haploid, or of a segregating population.

The invention further provides a method for the production of a lettuce plant resistant against TSWV and/or INSV by using a doubled haploid generation technique to generate a doubled haploid line which may comprise the said resistance.

The invention furthermore relates to hybrid seed that can be grown into a plant having resistance to TSWV and/or INSV and to a method for producing such hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid lettuce plant that is resistant against TSWV and/or INSV, which may comprise crossing a first parent lettuce plant with a second parent lettuce plant, and harvesting the resultant hybrid seed, of which the first parent plant and/or the second parent plant is resistant against TSWV and/or INSV, and growing said hybrid seeds into TSWV and/or INSV resistant hybrid plants.

The invention also relates to a method for the production of a lettuce plant resistant against TSWV and/or INSV by using a seed that may comprise a genetic determinant in its genome that leads to resistance to TSWV and/or INSV for growing the said lettuce plant. The seeds are suitably seeds of which a representative sample was deposited with the NCIMB under deposit number NCIMB 42023.

The invention also relates to a method for seed production which may comprise growing lettuce plants from seeds of which a representative sample was deposited with the NCIMB under deposit number NCIMB 42023, allowing the plants to produce seeds, and harvesting these seeds. Production of the seeds is suitably performed by crossing or selfing.

In one embodiment, the invention relates to a method for the production of a lettuce plant resistant against TSWV and/or INSV by using tissue culture.

The invention further relates to a method for the production of a lettuce plant resistant against TSWV and/or INSV by using vegetative reproduction.

In one embodiment, the invention relates to a method for the production of a lettuce plant resistant against TSWV and/or INSV by using a method for genetic modification to introgress the said resistance into the lettuce plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of lettuce plants that are resistant against TSWV and/or INSV wherein germplasm which may comprise said resistance is used. Representative seed of said plant which may comprise the genetic determinant and being representative for the germplasm was deposited with the NCIMB under deposit number NCIMB 42023.

In a further embodiment, the invention relates to a method for the production of a lettuce plant resistant against TSWV and/or INSV wherein progeny or propagation material of a plant which may comprise the genetic determinant conferring said resistance is used as a source to introgress the said resistance into another lettuce plant. Representative seed of said plant which may comprise the genetic determinant was deposited with the NCIMB under deposit number NCIMB 42023.

The invention provides preferably a lettuce plant resistant against TSWV and/or INSV, which plant is obtainable by any of the methods herein described and/or familiar to the skilled person.

The invention further provides a method for selecting a lettuce plant resistant against TSWV and/or INSV, which method may comprise screening plants for the aforementioned resistance(s) as herein described.

The invention also relates to the use of a genetic determinant conferring TSWV and/or INSV resistance, for producing a lettuce plant resistant against TSWV and/or INSV, which genetic determinant is as present in the genome of plants of which a representative sample was deposited with the NCIMB under deposit number NCIMB 42023.

Deposits

Representative seeds of *Lactuca sativa* containing the genetic determinant of the invention which confers resistance to TSWV and/or INSV were deposited under accession number NCIMB 42023 on 9 Aug. 2012 with NCIMB Ltd. (Ferguson Building, Craibstone Estate, Bucksburn, Aberdeen, AB21 9YA). All seeds of the deposit may comprise the genetic determinant homozygously. Plants grown from these seeds are thus highly resistant against TSWV and/or INSV.

The deposited seeds do not meet the DUS criteria which are required for obtaining plant variety protection, and can therefore not be considered to be a plant invention.

Sequence Data

TABLE 1

Sequence data of the SNP markers. In
NCIMB deposit 42023 the marker TSWV-00001
is linked to the genetic determinant
conferring resistance to TSWV and/or INSV.
Differences in nucleotide sequence between
the resistant and susceptible alleles for
each marker are indicted in square brackets
e.g.[resistant allele/susceptible allele].

| TSWV-00001 | TGCAGCGTATCCTCCGCATGCTCACTAGCTAT |
| Sequence ID | GGTGTTTT[T/C]AACGAACACATCATCTCCG |
| NO: 1 | GTGATATCTTACAACGAAGATA |

TABLE 1-continued

Sequence data of the SNP markers. In
NCIMB deposit 42023 the marker TSWV-00001
is linked to the genetic determinant
conferring resistance to TSWV and/or INSV.
Differences in nucleotide sequence between
the resistant and susceptible alleles for
each marker are indicted in square brackets
e.g.[resistant allele/susceptible allele].

| TSWV-00002 | TTAAGTTTATGAACCTCATTCGACAAAATGCC |
| Sequence ID | TTGTCAAT[T/C]ACTGAAAAGGAAAATGAAC |
| NO: 2 | TCCAAAATGTCAGATCAGAAC |

The present invention will be elucidated in the following examples. These examples are for illustrative purposes only and are not to be construed as limiting the present invention in any way.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Bioassay for TSWV and/or INSV

To test whether a plant is resistant against TSWV and/or INSV, a bioassay was performed. The TSWV and/or INSV bioassay can be performed as described herein.

Seeds were sown in peat cubes in the glass house. The plants were grown for 2 weeks at a temperature of 22° C.-28° C. A relevant number of plants per line were evaluated, e.g. 14 plants, so that segregation could be observed if present. The young plants were inoculated with a TSWV innoculum at growth stage 3 or 4. For TSWV, the plants were scored for infection 14 days post infection and at 21 days post infection.

As highly resistant plants of this invention, plants grown from seeds of *Lactuca sativa*, of which a representative sample was deposited under NCIMB accession number NCIMB 42023, were used for the bioassay. Plants from variety "Fabietto" and "Bambi" were also used in this bioassay as susceptible control plants.

Each plant was scored for the amount of TSWV symptoms, based on the scale explained in Table 2. The skilled person is not bound to using this scale but can also use a scale with another subdivision as long as the scoring is performed at the same plant growth stage. This will not influence the final results of the screening.

The scores of the TSWV bioassay are summarized in Table 3. It is clear from the results of the bioassay that all plants of the invention are resistant to TSWV.

TABLE 2

Scale used for Scoring of TSWV or INSV resistance and susceptibility.

| Score | TSWV OR INSV SYMPTOMS | GROWTH AS COMPARED TO CONTROL | |
|---|---|---|---|
| 1 | No symptoms/no damage | Comparable in size | RESISTANT |
| 2 | Weak local symptoms: round yellow lesions on the infected leaves | Moderately smaller in size | RESISTANT |

TABLE 2-continued

Scale used for Scoring of TSWV or INSV resistance and susceptibility.

| Score | TSWV OR INSV SYMPTOMS | GROWTH AS COMPARED TO CONTROL | |
|---|---|---|---|
| 3 | Medium: obvious symptoms present on leaves; leaves are mosaic or deformed | Noticeably smaller in size | SUSCEPTIBLE |
| 4 | Obvious symptoms present on leaves; Very stunted; leaves are mosaic or deformed | Considerably smaller in size | SUSCEPTIBLE |
| 5 | Death or very stunted; strong symptoms present | Considerably smaller in size | SUSCEPTIBLE |

TABLE 3

Score of TSWV-bioassay.

| Material | Total number of plants screened | Number of plants scored Resistant/Susceptible | TSWV |
|---|---|---|---|
| NCIMB 42023 | 38 | 38/0 | Resistant |
| Bambi | 14 | 0/14 | Susceptible |
| Fabietto | 14 | 0/14 | Susceptible |

Plants that were scored as being resistant against TSWV were also tested for resistance to INSV using a similar bioassay testing method. For INSV, the plants were scored for infection at 18, 24 and 30 days post infection.

The same scoring scale as outlined in Table 2 was also employed for the INSV testing.

The scores of the INSV bioassay are summarised in Table 4. It is clear from the results of the bioassay that all the plants of the invention are resistant to TSWV and/or INSV.

TABLE 4

Score of INSV-bioassay.

| Material | Total number of plants screened | Number of plants scored Resistant/Susceptible | INSV |
|---|---|---|---|
| NCIMB 42023 | 38 | 38/0 | Resistant |
| Bambi | 14 | 1/13 | Susceptible |
| Fabietto | 14 | 2/12 | Susceptible |

Additionally, ImmunoStrip tests (Agdia Inc., Elkhart, Ind., USA, 46514) for TSWV and INSV were used to confirm that those plants that were scored as being symptomless or resistant in the bioassays, also prevented viral multiplication or the accumulation of virus particles, following virus inoculation of the plant ImmunoStrip testing was performed, as per manufacturer's instructions, on young leaves of TSWV or INSV inoculated plants that were grown from seeds of *Lactuca sativa*, of which a representative sample was deposited under NCIMB accession number NCIMB 42023. ImmunoStrip testing was also performed on plants from lettuce variety "Fabietto" and "Bambi" that were inoculated with TSWV or INSV.

The interpretation of ImmunoStrip test results is detailed in the "User Guide: Agdia ImmunoStrip Test". A positive score indicates the presence of the virus being tested, while a negative score indicates the absence of the virus being tested. Furthermore, a negative score indicates that the viral titer is comparable to a non-virus infected plant.

The scores of the ImmunoStrip test for TSWV and INSV are summarized in Table 5. The results indicate that viral multiplication or accumulation is prevented in plants of the invention which may comprise a genetic determinant, which confers resistance to TSWV and/or INSV.

TABLE 5

Score of TSWV- and INSV- ImmunoStrip testing.

| Material | ImmunoStrip Test | Score |
|---|---|---|
| NCIMB 42023 | TSWV | Negative |
| Bambi | TSWV | Positive |
| Fabietto | TSWV | Positive |
| NCIMB 42023 | INSV | Negative |
| Bambi | INSV | Positive |
| Fabietto | INSV | Positive |

Example 2

Introgressing TSWV and/or INSV Resistance into a Susceptible Background

F1 plants of the invention were tested in a bioassay as described in Example 1. No highly TSWV and/or INSV resistant plants were observed.

From the F1 population, a plant was selfed to obtain a population of F2 seeds. Seventy-eight randomly chosen F2 plants were grown from these seeds and self-fertilised. The F3 lines were tested in a bioassay as described in Example 1. Resistance scores are summarized in Table 6.

The segregation of the F2 population demonstrates that the inheritance of the resistance of the invention is comparable with that of a monogenic trait (susceptible:heterozygous:resistant=1:2:1).

TABLE 6

Segregation of TSWV and/or INSV resistance.

| Susceptible F3-lines | Segregating F3-lines | Resistant F3-lines | Chi-Square Probability |
|---|---|---|---|
| 22 | 38 | 18 | 0.79 |

Example 3

Breeding for TSWV Resistance and/or INSV Resistance

A plant of the invention 08D.121730 grown from a seed of which a representative sample was deposited under NCIMB accession number NCIMB 42023, and which was resistant to TSWV and/or INSV according to the bioassay as described in Example 1, was crossed with a TSWV and INSV susceptible lettuce plant 08D.841822.

From the F1 population a plant 09D.120395 was selected and selfed to obtain a population of F2 plants. The F2 was tested for TSWV and INSV resistance according to the bioassay as described in Example 1.

The segregation of the F2 population demonstrated that the inheritance of the resistance of the invention was consistent with that of a monogenic trait and furthermore the segregation data confirmed the inheritance of TSWV and INSV resistance from the crossing plant 08D.121730.

From the F2 population a TSWV resistant plant 10D.20479 was selected and selfed to obtain a population of F3 plants. The F3 was tested for TSWV and INSV resistance according to the bioassay as described in Example 1.

Again, the segregation of the F3 population demonstrated that the resistance of the invention was consistent with that of a monogenic trait.

Finally, from the F3 population a TSWV and/or INSV resistant plant 11D.231349 was selected and selfed to obtain a population of F4 plants. The F4 was tested for TSWV and INSV resistance according to the bioassay as described in Example 1.

The F4 population showed no segregation of the resistance of the invention. This demonstrated that the F4 seed was in fact homozygous and uniform for the genetic determinant which confers resistance to TSWV and/or INSV.

The invention is further described by the following numbered paragraphs:

1. A lettuce plant (*Lactuca sativa* L.) comprising a genetic determinant, which when homozygously present confers resistance to tomato spotted wilt virus (TSWV) and/or impatiens necrotic spot virus (INSV), and which is as found in or obtainable from plants grown from seeds of which a representative sample was deposited under NCIMB accession number 42023.

2. A lettuce plant of paragraph 1, which is homozygous for the genetic determinant and resistant against TSWV and/or INSV.

3. A lettuce plant of paragraph 1 or paragraph 2, wherein said genetic determinant in the seeds of NCIMB deposit 42023 is located on linkage group 2 and linked to marker TSWV-00001 (SEQ ID NO: 1).

4. Seed comprising the genetic determinant as defined in any one of the paragraphs 1 to 3.

5. Seed of paragraph 4, wherein the plant grown from said seed is resistant against TSWV and/or INSV.

6. Progeny of a lettuce plant of any of the paragraphs 1 to 3, or progeny of plants grown from seeds of paragraph 4 or 5, wherein the progeny plant comprises the genetic determinant as defined in any one of the paragraphs 1 to 3.

7. Progeny plant of paragraph 6 wherein the progeny plant is resistant against TSWV and/or INSV.

8. Propagation material derived from a plant as paragraphed in any one of the paragraphs 1 to 3, wherein the propagation material comprises the genetic determinant as defined in any one of the paragraphs 1 to 3.

9. Propagation material capable of growing into a plant of any one of the paragraphs 1 to 3.

10. Propagation material of paragraph 8 or paragraph 9, wherein the propagation material is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

11. Tissue culture of propagation material as paragraphed in any of the paragraphs 8 to 10.

12. Part of a lettuce plant, of any one of the paragraphs 1 to 3, paragraph 6 or 7, which harvested part is in particular lettuce head and/or leaf, and optionally in processed form.

13. Part of a lettuce plant of paragraph 12, wherein the part is a food product or part thereof.

14. A nucleic acid molecule causative of resistance to TSWV and/or INSV, comprising a DNA sequence, which is linked to marker TSWV-00001 (SEQ ID NO: 1) located on linkage group 2, or a resistance conferring part of said nucleic acid molecule.

15. Nucleic acid molecule, or a resistance conferring part of said nucleic acid molecule of paragraph 14, comprising a DNA sequence, which is located between marker TSWV-00001 (SEQ ID NO: 1) and marker TSWV-00002 (SEQ ID NO: 2).

16. Use of the markers as defined in paragraph 3, and/or use of the nucleic acid molecule of paragraph 14 and/or paragraph 15, to identify or develop TSWV and/or INSV resistant plants, or develop other markers linked to the genetic determinant as defined in any one of the paragraphs 1 to 3.

\* \* \*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A lettuce plant (*Lactuca sativa* L.) comprising a genetic determinant, which when homozygously present confers resistance to tomato spotted wilt virus (TSWV) and/or impatiens necrotic spot virus (INSV), and which is as found in or obtainable from plants grown from seeds of which a representative sample was deposited under NCIMB accession number 42023.

2. A lettuce plant as claimed in claim 1, which is homozygous for the genetic determinant and resistant against TSWV and/or INSV.

3. A lettuce plant as claimed in claim 1, wherein said genetic determinant in the seeds of NCIMB deposit 42023 is located on linkage group 2 and linked to marker TSWV-00001 (SEQ ID NO: 1).

4. A seed comprising the genetic determinant as defined in claim 1.

5. The seed as claimed in claim 4, wherein the plant grown from said seed is resistant against TSWV and/or INSV.

6. A progeny of a lettuce plant grown from the seed as claimed in claim 4, wherein the progeny plant comprises a genetic determinant, which when homozygously present confers resistance to tomato spotted wilt virus (TSWV) and/or impatiens necrotic spot virus (INSV), and which is as found in or obtainable from plants grown from seeds of which a representative sample was deposited under NCIMB accession number 42023.

7. A progeny of a lettuce plant as claimed in claim 1, wherein the progeny plant comprises a genetic determinant, which when homozygously present confers resistance to tomato spotted wilt virus (TSWV) and/or impatiens necrotic spot virus (INSV), and which is as found in or obtainable from plants grown from seeds of which a representative sample was deposited under NCIMB accession number 42023.

8. The progeny plant as claimed in claim 7 wherein the progeny plant is resistant against TSWV and/or INSV.

9. Propagation material derived from a plant as claimed in claim 1, wherein the propagation material comprises the genetic determinant as defined in claim 1.

10. Propagation material as claimed in claim 9 wherein the propagation material is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

11. Tissue culture of propagation material as claimed in claim 9.

12. Propagation material capable of growing into a plant as claimed in claim 1.

13. Part of a lettuce plant, as claimed in claim 1 which harvested part is in particular lettuce head and/or leaf, and optionally in processed form.

14. The part of a lettuce plant as claimed in claim 13, wherein the part is a food product or part thereof.

* * * * *

SEQUENCE LISTING

```
<160> NUMBER OF SEQ ID NOS: 2

<210> SEQ ID NO 1
<211> LENGTH: 82
<212> TYPE: DNA
<213> ORGANISM: Lactuca sativa
<220> FEATURE:
<221> NAME/KEY: source
<222> LOCATION: 1..82
<223> OTHER INFORMATION: /organism="Lactuca sativa"
      /mol_type="unassigned DNA"
<220> FEATURE:
<221> NAME/KEY: variation
<222> LOCATION: 41
<223> OTHER INFORMATION: /replace="t"

<400> SEQUENCE: 1
```

```
tgcagcgtat cctccgcatg ctcactagct atggtgtttt caacgaacac atcatctccg     60
gtgatatctt acaacgaaga ta                                              82

<210> SEQ ID NO 2
<211> LENGTH: 81
<212> TYPE: DNA
<213> ORGANISM: Lactuca sativa
<220> FEATURE:
<221> NAME/KEY: source
<222> LOCATION: 1..81
<223> OTHER INFORMATION: /organism="Lactuca sativa"
      /mol_type="unassigned DNA"
<220> FEATURE:
<221> NAME/KEY: variation
<222> LOCATION: 41
<223> OTHER INFORMATION: /replace="t"

<400> SEQUENCE: 2
ttaagtttat gaacctcatt cgacaaaatg ccttgtcaat cactgaaaag gaaaatgaac     60
tccaaaatgt cagatcagaa c                                               81
```